US00PP29810P3

(12) United States Plant Patent
Feindura

(10) Patent No.: US PP29,810 P3
(45) Date of Patent: Nov. 6, 2018

(54) ***PELARGONIUM* PLANT NAMED 'PACPEIA'**

(50) Latin Name: ***Pelargonium* x *hortorum* X *Pelargonium peltatum***
Varietal Denomination: Pacpeia

(71) Applicant: Antonia Feindura, Dresden (DE)

(72) Inventor: Antonia Feindura, Dresden (DE)

(73) Assignee: ELSNER pac JUNGPFLANZEN GbR, Dresden (DE)

( * ) Notice: Subject to any disclaimer, the term of this patent is extended or adjusted under 35 U.S.C. 154(b) by 3 days.

(21) Appl. No.: 15/530,954

(22) Filed: Mar. 28, 2017

(65) Prior Publication Data

US 2018/0288919 P1 Oct. 4, 2018

(51) Int. Cl.
*A01H 5/02* (2018.01)

(52) U.S. Cl.
USPC ..... Plt./324

(58) Field of Classification Search
USPC ..... Plt./324
See application file for complete search history.

*Primary Examiner* — Anne Marie Grunberg
(74) *Attorney, Agent, or Firm* — C. A. Whealy

(57) ABSTRACT

A new and distinct interspecific Geranium plant named 'Pacpeia', characterized by its upright and uniformly rounded plant habit; moderately vigorous growth habit; freely basal branching habit; dark green-colored leaves; early and freely flowering habit; and large dark red-colored semi-double flowers that are held above the foliar plane on strong peduncles.

1 Drawing Sheet

Botanical designation: *Pelargonium* x *hortorum* X *Pelargonium peltatum.*

Cultivar denomination: 'PACPEIA'.

BACKGROUND OF THE INVENTION

The present invention relates to a new and distinct cultivar of interspecific Geranium plant, botanically known as *Pelargonium* x *hortorum* X *Pelargonium peltatum*, and hereinafter referred to by the cultivar name 'Pacpeia'.

The new interspecific Geranium plant is a product of a planned breeding program conducted by the Inventor in Dresden, Germany. The objective of the breeding program is to develop new uniform interspecific Geranium plants with attractive flower colors.

The new interspecific Geranium plant originated from a cross-pollination made by the Inventor in Dresden, Germany during the summer of 2013 of an unnamed proprietary selection of *Pelargonium* x *hortorum*, not patented, as the female, or seed, parent with an unnamed proprietary selection of *Pelargonium peltatum*, not patented, as the male, or pollen, parent. The new interspecific Geranium plant was discovered and selected by the Inventor as a flowering plant from within the progeny of the stated cross-pollination in a controlled greenhouse environment in Dresden, Germany during the spring of 2014.

Asexual reproduction of the new interspecific Geranium plant by vegetative terminal cuttings in a controlled greenhouse environment in Dresden, Germany since January, 2015 has shown that the unique features of this new interspecific Geranium plant are stable and reproduced true to type in successive generations.

SUMMARY OF THE INVENTION

Plants of the new interspecific Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pacpeia'. These characteristics in combination distinguish 'Pacpeia' as a new and distinct interspecific Geranium plant:

1. Upright and uniformly rounded plant habit.
2. Moderately vigorous growth habit.
3. Freely basal branching habit.
4. Dark green-colored leaves.
5. Early and freely flowering habit.
6. Large dark red-colored semi-double flowers that are held above the foliar plane on strong peduncles.

Plants of the new interspecific Geranium differ primarily from plants of the parent selections in plant habit as plants of the new interspecific Geranium are more uniform than plants of the parent selections.

Plants of the new interspecific Geranium can be compared to plants of the *Pelargonium* x *hortorum* X *Pelargonium peltatum* 'Pactiored', disclosed in U.S. Plant Pat. No. 28,384. In side-by-side comparisons, plants of the new interspecific Geranium differ from plants of 'Pactiored' in the following characteristics:

1. Plants of the new interspecific Geranium are not as outwardly spreading as plants of 'Pactiored'.
2. Plants of the new interspecific Geranium are not as vigorous as plants of 'Pactiored'.
3. Leaves of plants of the new interspecific Geranium do not have a discernible zonation pattern whereas leaves of plants of 'Pactiored' have a zonation pattern.
4. Plants of the new interspecific Geranium have larger flower umbels and flowers than plants of 'Pactiored'.

5. Plants of the new interspecific Geranium have semi-double type flowers whereas plants of 'Pactiored' have single-type flowers.

BRIEF DESCRIPTION OF THE PHOTOGRAPH

The accompanying colored photograph illustrates the overall appearance of the new interspecific Geranium plant showing the colors as true as it is reasonably possible to obtain in colored reproductions of this type. Colors in the photograph may differ slightly from the color values cited in the detailed botanical description which accurately describe the colors of the new interspecific Geranium plant.

The photograph comprises a side perspective view of a typical flowering plant of 'Pacpeia' grown in a container.

DETAILED BOTANICAL DESCRIPTION

The aforementioned photograph and following observations, measurements and values describe plants grown in 19-cm containers during the winter, spring and summer in a glass-covered greenhouse in Dresden, Germany and under cultural practices typical of commercial interspecific Geranium production. During the production of the plants, day temperatures averaged 18° C., night temperatures averaged 16° C. and light levels ranged from 15 kilolux to 100 kilolux. Plants were three months old when the photograph was taken and nine months old when the detailed description was taken. In the detailed description, color references are made to The Royal Horticultural Society Colour Chart, 1995 Edition, except where general terms of ordinary dictionary significance are used.

Botanical classification: *Pelargonium* x *hortorum* X *Pelargonium peltatum* 'Pacpeia'.

Parentage:

*Female, or seed, parent*.—Unnamed proprietary selection of *Pelargonium* x *hortorum*, not patented.

*Male or pollen parent*.—Unnamed proprietary selection of *Pelargonium peltatum*, not patented.

Propagation:

*Type*.—By vegetative terminal cuttings.

*Time to initiate roots, summer*.—About 18 days at temperatures about 20° C.

*Time to initiate roots, winter*.—About 22 days at temperatures about 20° C.

*Time to produce a rooted young plant, summer*.—About four weeks at temperatures about 20° C.

*Time to produce a rooted young plant, winter*.—About four weeks at temperatures about 18° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Upright and uniformly rounded plant habit; inverted triangle; densely foliated; moderately vigorous growth habit; moderate growth rate; freely basal branching habit with about 28 lateral branches developing per plant; pinching is not required.

*Plant height, to top of umbels*.—About 30 cm.

*Plant height, to top of foliar plane*.—About 25 cm.

*Plant width*.—About 45 cm.

*Lateral branches*.—Length: About 25 cm. Diameter: About 6 mm. Internode length: About 1.5 cm. Texture: Pubescent. Color: Close to 146B.

Leaf description:

*Arrangement*.—Opposite and alternate; simple.

*Length*.—About 5 cm.

*Width*.—About 8.1 cm.

*Shape*.—Rounded; roughly reniform.

*Apex*.—Rounded.

*Base*.—Cordate, open.

*Margin*.—Bi-crenate.

*Venation pattern*.—Palmate.

*Texture, upper and lower surfaces*.—Sparsely pubescent; velvety.

*Color*.—Developing and fully expanded leaves, upper surface: Close to 137A; venation, close to 137A. Developing and fully expanded leaves, lower surface: Close to 147B; venation, close to 146B. Zonation pattern: Not discernible.

*Petioles*.—Length: About 6 cm. Diameter: About 2 mm. Texture, upper and lower surfaces: Pubescent; rough. Color, upper and lower surfaces: Close to 147B.

Flower description:

*Flower arrangement and flowering habit*.—Large semi-double flowers arranged in roughly hemispherical umbels arising from apical leaf axils; umbels displayed above the foliar plane on strong peduncles; flowers face upright to outwardly; freely flowering habit with about 23 flower buds and flowers per umbel and about 42 umbels developing per plant.

*Fragrance*.—None detected.

*Flowering season*.—Early flowering habit; plants begin flowering about 70 days after planting; in the garden in Germany, flowering begins in April and continues until frost in the autumn.

*Flower longevity*.—Flowers last about six to ten days on the plant; umbels last about three to four weeks on the plant; flowers persistent.

*Umbel height*.—About 5 cm.

*Umbel diameter*.—About 11 cm.

*Flower diameter*.—About 5 cm.

*Flower depth (height)*.—About 1.5 cm.

*Flower buds*.—Length: About 7 mm. Diameter: About 5 mm. Shape: Round. Color: Close to 144A.

*Petals and petaloids*.—Quantity per flower: About ten; imbricate. Length: About 2.7 cm. Width: About 1.9 cm. Shape: Obovate. Apex: Rounded. Base: Cuneate. Margin: Entire. Texture, upper and lower surfaces: Smooth, glabrous; velvety. Color: When opening and fully opened, upper surface: Darker than 45A; venation, close to 187A; color does not change with development. When opening and fully opened, lower surface: Close to 46B; venation, close to 46B; color does not change with development.

*Sepals*.—Quantity per flower: Five arranged in a single whorl. Length: About 1.1 cm. Width: About 3 mm. Shape: Lanceolate. Apex: Acute. Margin: Entire. Texture, upper and lower surfaces: Pubescent. Color, upper and lower surfaces: Distally, close to 144A; proximally, close to 183A.

*Peduncles* (*umbel stems*).—Length: About 11.5 cm. Diameter: About 3 mm. Strength: Strong. Angle: Mostly upright. Texture: Pubescent. Color: Close to 144A.

*Pedicels* (*individual flower stems*).—Length: About 2.5 cm. Diameter: About 1 mm. Strength: Moderately strong; flexible. Texture: Pubescent. Color: Close to 183A.

*Reproductive organs*.—Androecium: Stamen quantity per flower: About twelve. Anther length: About 2 mm. Anther shape: Tubular. Anther color: Close to 187A. Pollen amount: Moderate. Pollen color: Close to 167A. Gynoecium: Pistil quantity per flower: One. Pistil length: About 8 mm. Stigma shape: Five-parted. Stigma color: Close to 60A. Style length: About 2 mm. Style color: Close to 58A. Ovary color: Close to 139D. Seeds and fruits: Seed and fruit development have not been observed on plants of the new interspecific Geranium.

Disease & pest resistance: Plants of the new interspecific Geranium have not been observed to be resistant to pathogens and pests common to interspecific Geraniums.

Temperature tolerance: Plants of the new interspecific Geranium have been observed to tolerate temperatures ranging from about 1° C. to about 35° C.

It is claimed:

1. A new and distinct interspecific Geranium plant named 'Pacpeia' as illustrated and described.

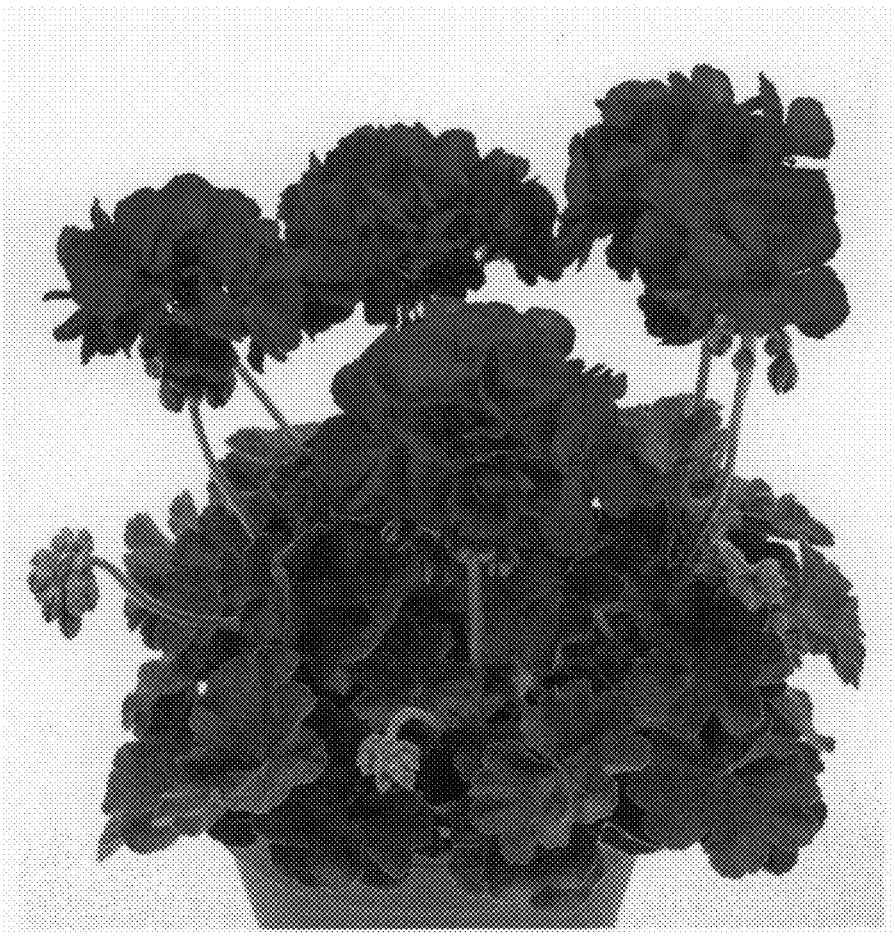

* * * * *